United States Patent
Zwicker et al.

(10) Patent No.: US 12,403,123 B2
(45) Date of Patent: Sep. 2, 2025

(54) METHOD FOR TREATING SICKLE CELL DISEASE USING QUERCETIN-CONTAINING COMPOSITIONS

(71) Applicant: Beth Israel Deaconess Medical Center, Inc., Boston, MA (US)

(72) Inventors: Jeffrey I. Zwicker, Boston, MA (US); Bruce Furie, Boston, MA (US); Robert Flaumenhaft, Boston, MA (US)

(73) Assignee: BETH ISRAEL DEACONESS MEDICAL CENTER, INC., Boston, MA (US)

( * ) Notice: Subject to any disclaimer, the term of this patent is extended or adjusted under 35 U.S.C. 154(b) by 0 days.

(21) Appl. No.: 17/865,609

(22) Filed: Jul. 15, 2022

(65) Prior Publication Data

US 2023/0029216 A1    Jan. 26, 2023

Related U.S. Application Data

(60) Provisional application No. 63/222,640, filed on Jul. 16, 2021.

(51) Int. Cl.
| | |
|---|---|
| *A61K 31/352* | (2006.01) |
| *A61K 31/375* | (2006.01) |
| *A61K 31/455* | (2006.01) |
| *A61K 31/519* | (2006.01) |
| *A61P 7/06* | (2006.01) |

(52) U.S. Cl.
CPC .......... *A61K 31/352* (2013.01); *A61K 31/375* (2013.01); *A61K 31/455* (2013.01); *A61K 31/519* (2013.01); *A61P 7/06* (2018.01)

(58) Field of Classification Search
CPC .... A61K 45/06; A61K 31/375; A61K 31/455; A61K 31/352; A61K 31/519; A61K 31/7048; A61K 31/45; A61P 7/06
See application file for complete search history.

(56) References Cited

U.S. PATENT DOCUMENTS

| | | | |
|---|---|---|---|
| 5,626,884 A | 5/1997 | Lockett | |
| 6,121,249 A | 9/2000 | Weissman et al. | |
| 6,147,054 A * | 11/2000 | De Paoli Ambrosi | A61K 36/185 514/474 |
| 7,745,486 B2 * | 6/2010 | Lines | A61P 35/02 514/474 |
| 8,840,950 B2 | 9/2014 | Hibbert et al. | |
| 8,901,109 B2 | 12/2014 | Lines | |
| 9,987,247 B2 | 6/2018 | Liu et al. | |
| 10,391,096 B2 * | 8/2019 | Lines | A61K 45/06 |
| 11,872,241 B2 | 1/2024 | Zwicker et al. | |
| 2006/0276393 A1 | 12/2006 | Milburn et al. | |
| 2007/0248590 A1 | 10/2007 | Milne et al. | |
| 2011/0224290 A1 | 9/2011 | Estrela Ariquel et al. | |
| 2013/0028864 A1 | 1/2013 | Theoharides | |
| 2013/0095095 A1 | 4/2013 | Lines | |
| 2014/0350129 A1 | 11/2014 | Sikora et al. | |
| 2015/0366838 A1 | 12/2015 | Lines | |
| 2016/0287591 A1 | 10/2016 | Lorence et al. | |
| 2024/0133897 A1 | 4/2024 | Zwicker et al. | |

FOREIGN PATENT DOCUMENTS

| | | |
|---|---|---|
| WO | 2000012085 A1 | 3/2000 |
| WO | 2006076681 A2 | 7/2006 |
| WO | 2008011363 A2 | 1/2008 |
| WO | 2008011364 A2 | 1/2008 |
| WO | 2012174282 A2 | 12/2012 |
| WO | 2015125137 A1 | 8/2015 |
| WO | 2017083281 A1 | 5/2017 |
| WO | 2022020659 A1 | 1/2022 |
| WO | 2022023380 A2 | 2/2022 |
| WO | 2023288044 A1 | 1/2023 |

OTHER PUBLICATIONS

Faes et al., "Red blood cells modulate structure and dynamics of venous clot formation in sickle cell disease", 2019, Blood, 133(3), pp. 2529-2541. (doi.org/10.1182/blood.2019000424) (Year: 2019).*
Gregory J. Kato, "Sickle cells and sickle trait in thrombosis", 2019, Blood, 133(3), p. 2463. (doi.org/10.1182/blood.2019000694) (Year: 2019).*
Ay et al. "High Plasma Levels of Soluble P-selectin are Predictive of Venous Thromboembolism in Cancer Patients: Results from the Vienna Cancer and Thrombosis Study (CATS)" Oct. 1, 2018, Blood 112(7):2703-2708.
Baaten et al. "A synthesis Approach of Mouse Studies to Identify Genes and Proteins in Arterial Thrombosis and Bleeding" Oct. 1, 2018, Blood 132(24):35-46, XP055836634.
Crespy et al. "Quercetin, but not Its Glycosides, Is Absorbed from the Rat Stomach" 2002, J. Agricultural and Food Chemistry 50:618-621.
Curran et al. "Western New England University and Quercis Pharma Sign Exclusive Worldwide License Agreements" Quercis Pharma AG, News Release, May 19, 2021 (4 pages).
Dai et al. "Effects of Quercetin on Coagulation Function in Model Mice with Acute Lymphoblastic Leukemia" Jun. 27, 2018, J. Emergency in Traditional Chinese Medicine 27(6):970-973 (Chinese with full English translation).
Disanto et al. "Resveratrol and Quercetin Down-Regulate Tissue Factor Expression by Human Stimulated Vascular Cells" 2003, J. Thrombosis and Haemostasis 1:1089-1095.

(Continued)

*Primary Examiner* — Kevin E Weddington
(74) *Attorney, Agent, or Firm* — DLA Piper LLP (US)

(57) ABSTRACT

Disclosed are compositions and methods for treating sickle cell disease. Also disclosed are methods of treating sickle cell disease comprising administering to a subject in need thereof an effective amount of isoquercetin, vitamin B3, vitamin C, and optionally folic acid and wherein the effective amount is sufficient to halt progression of one or more of the symptoms of sickle cell disease.

11 Claims, No Drawings

(56) References Cited

OTHER PUBLICATIONS

European Search Report and Written Opinion for EP 19891072.1 recieved Jul. 8, 2022, 17 Pages.
International Search Report and Written Opinion for PCT/US2022/37259 dated Oct. 19, 2022.
McDowell et al. "Anthropometric Reference Data for Children and Adults: United States, 2003-2006" Oct. 22, 2008, National Health Statistics Reports, retrieved from the internet: https://www.cdc.gov/nchs/data/nhsr/nhsr010.pdf No. 10:45 Pages.
Middleton et al. "The Effects of Plant Flavonoids on Mammalian Cells: Implications for Inflammation, Heart Disease, and Cancer" Jan. 1, 2000, Pharmacological Reviews, American Society For Pharmacology and Experimental Therapeutics, United States 52(4):673-751, ISSN: 0031-6997, XP008047405.
Oh et al. "Dual Roles of Quercetin in Platelets: Phosphoinositide-3-Kinase and MAP Kinases Inhibition, and cAMP-Dependent Vasodilator-Stimulated Phosphoprotein Stimulation" 2012, Evidence-Based Complementary and Alternative Medicine 2012:1-10, Article ID. 485262.
Rakel "Integrative Medicine Second Ed." 2007, Botanical supplements Elsevier Saunders, 313-316.
Spittle "The Action of Vitamin C on Blood Vessels" Sep. 1974, American Heart J. Smoking and Health Bulletin 88(3): 387-388.
Staedler et al. "Drug Combinations with Quercetin: Doxorubicin Plus Quercetin in Human Breast Cancer Cells" Mar. 13, 2011, Cancer Chemotherapy and Pharmacology, Springer, Berlin, Germany 68(5):1161-1172, DOI: 10.1007/S00280-011-1596-X, ISSN: 1432-0843, XP019977320.
Stopa et al. "Protein Disulfide Isomerase Inhibition Blocks Thrombin Generation in Humans by Interfering with Platelet Factor V Activation" Jan. 12, 2017, JCI Insight 2(1):e89373.
Invitation to Pay Additional Fees for PCT/IB2023/054726 dated Jul. 18, 2023.
Ay et al. "Prediction of Venous Thromboembolism in Cancer Patients" Jul. 6, 2010, Blood 116(24):5377-5382.
Ay et al. "Prediction of Venous Thromboembolism in Patients With Cancer by Measuring Thrombin Generation: Results From the Vienna Cancer and Thrombosis Study" May 20, 2011, Journal of Clinical Oncology 29(15):2099-2103.
Bennish et al. "Hypoglycemia During Diarrhea in Childhood" May 10, 1990, New England Journal of Medicine 322(19):1357-1363.
Bors et al. "Flavanoids and Polyphenols: Chemistry and Biology" 1996, Handbook of Antioxidants, pp. 409-416.
Braga et al. "Drugs that inhibit TMEM16 proteins block SARS-CoV-2 spike-induced syncytia" Jun. 1, 2021, Nature, 594(7861):1-43.
Campigotto et al. "Biased Estimation of Thrombosis Rates in Cancer Studies Using the Method of Kaplan and Meier" Jul. 2012, J. Thromb. Haemost. 10(7):1449-1451.
Clinical Study NCT02195232 "Cancer Associated Thrombosis and Isoquercetin (CATIQ)" version 6 of Jan. 19, 2017, https://www.clinicaltrials.gov/study/NCT02195232?tab=history&a=6.
European Search Report and Written Opinion for EP 12840824.2 received May 21, 2015, 42 Pages.
European Search Report and Written Opinion for EP 21186637.1 received Dec. 3, 2021, 14 Pages.
European Search Report and written opinion for EP15810201.2 received May 24, 2018, 17 Pages.
European Supplemental Search Report and Written Opinion for EP 20897805.6 dated Oct. 13, 2023.
Feng et al., Sep. 30, 2013, Modern Clinical Laboratory Diagnostic Manual, Sichuan Science and Technology Press, p. 275 (in Chinese).
Harlow E., et al., "Antibody-Antigen Interactions: Structure of the Antibody-Antigen Complex," A Laboratory Manual, Cold Spring Harbor Laboratory Press, 1999, pp. 24-27, 7 Pages.
Holbrook et al. "Zafirlukast is a broad-spectrum thiol isomerase inhibitor that inhibits thrombosis without altering bleeding times" 2021, British Pharmacological Society, 178:550-563.
International Search Report and Written Opinion for application No. PCT/US2023/083669 dated Jun. 21, 2024.
Invitation to Pay Additional Fees for PCT/2023/083669 dated Apr. 2, 2024, 3 Pages.
Jurk et al. "Extracellular Protein Disulfide Isomerase Regulates Feedback Activation of Platelet Thrombin Generation Via Modulation of Coagulation Factor Binding" Dec. 2011 J. Thromb. Haemost. 9(11):2278-2290.
Kim et al. "Platelet Protein Disulfide Isomerase is Required for Thrombus Formation But Not for Hemostasis in Mice" Aug. 8, 2013, Blood 122(6):1052-1061.
Liu F et al. "Enhanced efficacy and reduced hepatotoxicity by combination of gnaphalium affine extract and benzbromarone in the treatment of rats with hyperuricemic nephropathy" 2021, Pharmaceutical Fronts, 3(3):e129-e137.
March Advanced Organic Chemistry: Reactions, Mechanisms and Structure, 1992, 6th Edition (Wiley-Interscience, New York) (Cover and TOC only).
McMahon et al. "Thrombotic and bleeding complications associated with chemotherapy" 2012, Semin Thromb Hemost 38(08):808-817.
Meyer et al. "Diagnostic Value of Two Rapid and Individual D-Dimer Assays in Patients with Clinically Suspected Pulmonary Embolism: Comparison with Microplate Enzyme-linked Immunosorbent Assay" Oct. 1998, Blood Coagulation & Fibrinolysis 9(7):603-608 (abstract only).
Partial Supplementary European Search Report and Written Opinion for EP 15810201.2 received Jan. 2, 2018, 13 Pages.
Schulman et al. "Definition of Major Bleeding in Clinical Investigations of Antihemostatic Medicinal Products in Non-Surgical Patients" Apr. 2005, J. Thromb. Haemost. 3(4):692-694.
Wu et al., "[42] Receptor-Mediated Transport of DNA into Eukaryotic Cells," Methods in Enzymology, Academic Press Inc., 1993, vol. 217, pp. 618-644.
Zwicker et al. "Prediction and Prevention of Thromboembolic Events with Enoxaparin in Cancer Patients with Elevated Tissue Factor-Bearing Microparticles: a Randomized-Controlled Phase II Trial (the Microtec Study)" Feb. 2013, Br. J. Haematol. 160(4):530-537.
Magalingam et al. "Protective Effects of Quercetin Glycosides, Rutin, and Isoquercetrin Against 6-hydroxydopamine (6-OHDA)-Induced Neurotoxicity in Rat Pheochromocytoma (PC-12) Cells," International Journal of Immunopathology and Pharmacology, Mar. 2016, 29(1):30-39.
Canadian Office Action for application No. CA 3,161,320 dated Oct. 7, 2024.
Extended European Search Report and Written Opinion for EP 20897805.6 dated Jan. 23, 2024.
Extended European Search Report and Written Opinion for application No. EP 22842916.3 dated Apr. 3, 2025.
OKPALA "Investigational Selectin-Targeted Therapy of Sickle Cell Disease" Sep. 22, 2014, Expert Opinion on Investigational Drugs, 24(2):229-238.
Zwicker et al. "Targeting Protein Disulfide Isomerase with the Flavonoid Isoquercetin to Improve Hypercoagulability in Advanced Cancer" Feb. 21, 2019, JCI Insight 4(4): 1-12.

\* cited by examiner

METHOD FOR TREATING SICKLE CELL DISEASE USING QUERCETIN-CONTAINING COMPOSITIONS

CROSS REFERENCE TO RELATED APPLICATIONS

This application claims the benefit under 35 U.S.C. § 119(e) of U.S. Provisional Patent Application No. 63/222,640, filed Jul. 16, 2021. The contents of these applications are incorporated herein by reference in their entireties for all purposes.

GOVERNMENT INTERESTS

This invention was made with government support under HL136394 and HL112302 awarded by the National Institutes of Health. The government has certain rights in the invention.

SUMMARY

The present disclosure relates to a method of sickle cell disease, the method comprising administering to subject in need thereof an effective amount of quercetin, vitamin B3, vitamin C and optionally folic acid.

Definitions

As used herein, "sickle cell disease" refers to a group of inherited red blood cell disorders that affect hemoglobin, the protein that carries oxygen through the body. Subjects with sickle cell disease have red blood cells that are crescent or "sickle" shaped and do not bend or move easily and can block blood flow throughout the body. Patients with sickle cell disease have abnormal hemoglobin called "hemoglobin S" or "sickle hemoglobin." The types of sickle cell disease include: hemoglobin Sβ0 thalassemia, hemoglobin Sβ+ thalassemia, hemoglobin SC, hemoglobin SD, hemoglobin SE, hemoglobin SS (or sickle cell anemia).

As used herein, "quercetin" refers to both quercetin aglycone and quercetin derivatives, e.g., quercetin-3-O-glucoside (also known as "isoquercetin", and referred to herein as "IsoQ", "IsoQ" or "Iso-Q"), quercetin-5-O-glucoside, quercetin-7-O-glucoside, quercetin-9-O-glucoside, quercetin-3'-O-glucoside, quercetin-4'-O-glucoside, quercetin-3-O-rutinoside (also known as rutin), quercetin-3-O-[a-rhamnosyl-(1->2)-a-rhamnosyl-(1->6)]-I3-glucoside, quercetin-3-O-galactoside, quercetin-7-O-galactoside, quercetin-3-O-rhamnoside, quercetin-7-O-galactoside, quercetin-glycoside, 7-hydroxyflavone, and any pharmaceutically acceptable salts thereof. "Quercetin" may also refer to isoquercetin or rutin or any constituent of rutin or isoquercetin, or metabolite or rutin or isoquercetin or quercetin, whether sulphated, glucuronidated or methylated form of rutin or quercetin, and any pharmaceutically acceptable salts thereof.

As used herein, "Vitamin B3" refers to vitamin B3 in its various forms, including, but not limited to niacinamide, nicotinic acid, nicotinamide, inositol hexaniacinate, or any combination thereof.

As used herein, "Vitamin C" refers to vitamin C including but not limited to L-ascorbic acid, D-ascorbic acid, or both and its salts (e.g., sodium ascorbate) or any combination thereof.

As used herein, "Folic acid" refers to a B vitamin including, but not limited to vitamin B9, folate, pteroylglutamic acid, and L-methyl folate, 5-MTHF (5-methyltetrahydrofolate) or any combination thereof.

As used herein, the term "pharmaceutical agent" or "compound" refers to a chemical entity or biological product, or a combination of chemical entities or biological products, administered to a person to treat or prevent or control a disease or condition.

The term "active agent", as used herein, means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline (i.e., amorphous) forms, and any polymorphs of the compound are included. All forms are contemplated herein regardless of the methods used to obtain them.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH2)_n$—COOH where n is 0-4, and the like. Lists of additional suitable salts may be found, e.g., in Remington's Pharmaceutical Sciences, 17th ed., Mack Publishing Company, Easton, Pa., p. 1418 (1985).

As used herein, the term "about" when immediately preceding a numerical value means a range of plus or minus 10% of that value, for example, "about 50" means 45 to 55, "about 25,000" means 22,500 to 27,500, etc., unless the context of the disclosure indicates otherwise, or is inconsistent with such an interpretation.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. An exemplary dosage form is a solid oral dosage form.

The term "pharmaceutical compositions", as used herein, are compositions comprising at least one active agent or a pharmaceutically acceptable salt thereof, and at least one other substance, such as a carrier. Pharmaceutical compositions meet the U.S. FDA's GMP (good manufacturing practice) standards for human or non-human drugs. The pharmaceutical compositions can be formulated into a dosage form.

The term "carrier", as used herein, applied to pharmaceutical compositions refers to a diluent, excipient, or vehicle with which an active agent is provided. The term "carrier", as used herein, applied to pharmaceutical compositions refers to a diluent, excipient, or vehicle with which an active agent is provided. Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional additional active agent may be included in a pharmaceutical composition, which do not substantially interfere with the activity of the active agent. The amount of carrier employed in conjunction with the compound is sufficient to provide a practical quantity of material for administration per unit dose of the active agent. Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the active agent.

The term "patient" or "subject" as used herein, is a human or non-human animal in need of medical treatment. Medical treatment can include treatment of an existing condition, such as a disease or disorder, prophylactic or preventative treatment, or diagnostic treatment. In some embodiments the patient is a human patient.

As used herein, the terms "administer," "administering" or "administration" as used herein refer to directly administering a compound or a composition to a subject.

The term "providing", as used herein, means giving, administering, selling, distributing, transferring (for profit or not), manufacturing, compounding, or dispensing.

The term "providing an extracellular thiol isomerase inhibitor compound or pharmaceutically acceptable salt thereof with at least one additional therapeutic agent", as used herein, means an active agent or pharmaceutically acceptable salt thereof and the additional active agent(s) are provided simultaneously in a single dosage form, provided concomitantly in separate dosage forms, or provided in separate dosage forms for administration separated by some amount of time that is within the time in which both the active agent or pharmaceutically acceptable salt thereof and the at least one additional active agent are within the blood stream of a patient. The active agent or pharmaceutically acceptable salt thereof and the additional active agent need not be prescribed for a patient by the same medical care worker. The additional active agent or agents need not require a prescription. Administration of the active agent or pharmaceutically acceptable salt thereof or the at least one additional active agent can occur via any appropriate route, for example, oral tablets, oral capsules, oral liquids, inhalation, injection, suppositories or topical contact.

The term "treatment", as used herein, includes providing an active agent or pharmaceutically acceptable salt thereof, either as the only active agent or together with at least one additional active agent sufficient to: (a) prevent a disease or condition or a symptom of a disease or condition from occurring in a patient who may be predisposed to the disease or condition but has not yet been diagnosed as having it; (b) inhibiting the disease or condition, i.e. arresting its development; and (c) relieving the disease or condition, i.e., causing regression of the disease or condition. "Treating" and "treatment" also means providing a therapeutically effective amount of an active agent or pharmaceutically acceptable salt thereof, as the only active agent or together with at least one additional active agent to a patient suffering from a disease or condition influenced by the activity of one or more active agents. "A disease or condition influenced by the activity of one or more active agents" means the one or more active agents is implicated in the disease or condition.

As used herein, the term "effective amount" refers to an amount that results in measurable inhibition of at least one symptom or parameter of a specific disorder or pathological process. As used herein the term "therapeutically effective amount" of compositions of the application is an amount, which confers a therapeutic effect on the treated subject, at a reasonable benefit/risk ratio applicable to any medical treatment. The therapeutic effect may be objective (that is, measurable by some test or marker) or subjective (that is, subject gives an indication of or feels an effect or physician observes a change).

The term "therapeutically effective amount" of an active agent, as used herein, means an amount effective, when administered to a patient, to provide a therapeutic benefit such as a prevention, inhibition, or an amelioration of symptoms, e.g., to prevent the activation of mast cells and prevent the formation of mast cell activated cytokines in a patient suffering from, sickle cell disease. A therapeutically effective amount may vary according to factors such as the health, age, and weight of the patient, and the ability of the compound to elicit a desired response in the patient. Dosage regimens may be adjusted to provide the optimum therapeutic response. A therapeutically effective amount is also one in which any toxic or detrimental effects (e.g., side effects) of the active agent are outweighed by the therapeutically beneficial effects.

The term "synergistic effect" as used herein, refers to an interaction or cooperation giving rise to a whole that is greater than the simple sum of its parts. As used herein, the effect of isoquercetin or quercetin with vitamin B3 and vitamin C produces results that are greater than either quercetin or vitamins B3 and C alone.

The term "preventing" may be taken to mean to prevent a specific disorder, disease or condition and/or prevent the reoccurrence of a specific disorder, disease or condition.

As used herein, the term "prognosis" means the probable course and outcome of a disease, especially of the chances of recovery.

As used herein the terms "treat", "treatment", "treated", or "treating" refer to both therapeutic treatment and prophylactic or preventative measures, wherein the object is to protect against (partially or wholly) or slow down (for example, lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include, but are not limited to, alleviation of symptoms; diminishment of the extent or vigor or rate of development of the condition, disorder or disease; stabilization (that is, not worsening) of the state of the condition, disorder or disease; delay in onset or slowing of the progression of the condition, disorder or disease; amelioration of the condition, disorder or disease state; and remission or recurrence (whether partial or total), whether or not it translates to immediate lessening of actual clinical symptoms, or enhancement or improvement of the condition, disorder or disease; preventing spread of the condition, disorder or disease state. Treatment seeks to elicit a clinically significant response without excessive levels of side effects. The term "unit dosage form" refers to physically discrete units suitable as a unitary dosage for human subjects and other animals, each unit containing a predetermined quantity of active material calculated to produce the desired therapeutic effect, in association with a suitable pharmaceutical excipient.

The terms "improving," "enhancing," "treating," and "lowering" refer to the administration of an effective amount of a composition of the invention to a subject, who needs to improve one or more of the above-mentioned conditions or has one or more of the just-mentioned disorders, or a symptom or a predisposition of one of more of the disorders or conditions, with the purpose to improve one or more of these conditions, or to prevent, cure, alleviate, relieve, remedy, or ameliorate one or more of these disorders, or the symptoms or the predispositions of one or more of them. The term "administration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intra-synovial, intrasternal, intranasal, intrathecal, intralesional, and intracranial injection, as well as various infusion techniques. An "effective amount" refers to a dose of the composition that is sufficient to provide a physical benefit (e.g., improving endurance) or a therapeutic benefit (e.g., lowering cholesterol or C-reactive protein levels, or reducing the risk of atherosclerosis or heart diseases). Both in vivo and in vitro studies can be conducted to determine optimal administration routes and doses.

The term "disease" as used herein is intended to be generally synonymous, and is used interchangeably with, the terms "disorder," "dysfunction," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a medical condition or disorder described in the present disclosure. Such administration encompasses co-administration of these therapeutic agents in a substantially simultaneous manner, such as in a single capsule, or dosage presentation, having a fixed ratio of active ingredients or in multiple, separate capsules for each active ingredient. In addition, such administration also encompasses use of each type of therapeutic agent in a sequential manner in the same patient, with delivery of the individual therapeutics separated by 1-24 hours, 1-7 days, or 1 or more weeks. In either case, the treatment regimen will provide beneficial effects of the drug combination in treating the conditions or disorders described herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

DETAILED DESCRIPTION

Various methods are described herein for the treatment of sickle cell disease or a related disorder selected from hemoglobin Sβ0 thalassemia, hemoglobin Sβ+ thalassemia, hemoglobin SC, hemoglobin SD, hemoglobin SE, hemoglobin SS (or sickle cell anemia). The methods include administration of at least one pharmaceutical composition to the subject. The treatment can reduce or eliminate the symptoms of sickle cell disease. The treatment can halt further progression of the symptoms of sickle cell disease. The treatment can slow further progression of the symptoms of sickle cell disease.

In one embodiment, the present invention describes a method of treating sickle cell disease, the method comprising administering to a subject in need thereof an effective amount of isoquercetin, vitamin B3, and vitamin C. The composition of this invention can be in various forms. In some embodiments, isoquercetin, vitamin B3, and vitamin C are administered in a single formulation. In some embodiments, isoquercetin, vitamin B3, and vitamin C are administered separately. In some embodiments, isoquercetin, vitamin B3, and vitamin C are administered in one or more formulation, wherein any one of isoquercetin, vitamin B3, and vitamin C may be administered in combination or alone. In some embodiment, the composition comprises folic acid. In some embodiments, isoquercetin, vitamin B3, and vitamin C are administered separately from folic acid.

This invention is based, at least in part, on the unexpected findings that a composition comprising isoquercetin, vitamin B3, vitamin C, and optionally folic acid as active ingredients exhibit synergistic effects in treating patients with sickle cell disease compared to treatment with either isoquercetin or quercetin alone. Extracellular protein disulfide isomerase (PDI) plays a critical role in the regulation of neutrophil recruitment, platelet activation and fibrin formation. These processes are implicated in the thrombo-inflammatory vasculopathy in sickle cell disease. Quercetin and isoquercetin are known to protect against thrombo-inflammatory vasculopathy. Moreover, the inventors have observed the surprising result that the combination of isoquercetin with vitamin B3 and vitamin C, as well as optionally with folic acid act synergistically to treat sickle cell disease and reduce symptoms in subjects. The composition comprising isoquercetin, vitamin B3, vitamin C, and optionally folic acid represents a surprising and substantial improvement in the treatment of sickle cell disease in subjects.

In one embodiment, the present invention describes a method of treating sickle cell disease, the method comprising administering to a subject in need thereof an effective amount of a protein disulfide isomerase (PDI) inhibitor, vitamin B3, and vitamin C. The composition of this invention can be in various forms. In some embodiments, PDI inhibitor, vitamin B3, and vitamin C are administered in a single formulation. In some embodiments, PDI inhibitor, vitamin B3, and vitamin C are administered separately. In some embodiments, PDI inhibitor, vitamin B3, and vitamin C are administered in one or more formulation, wherein any one of PDI inhibitor, vitamin B3, and vitamin C may be administered in combination or alone. In some embodiment, the composition comprises folic acid. In some embodiments, PDI inhibitor, vitamin B3, and vitamin C are administered separately from folic acid.

Pharmaceutical Compositions

In some embodiments, a method of treating sickle cell disease, the method comprising administering to a subject in need thereof an effective amount of isoquercetin, vitamin B3, and vitamin C. In some embodiments, a method of treating sickle cell disease, the method comprising administering to a subject in need thereof an effective amount of isoquercetin, vitamin B3, and vitamin C, wherein the composition further comprises folic acid.

In some embodiments, a method of treating sickle cell disease, the method comprising administering to a subject in need thereof an effective amount of isoquercetin, vitamin B3, vitamin C, and optionally folic acid, wherein the composition includes about 250 mg to about 1000 mg of isoquercetin. In some embodiments, the composition includes about 20 μg to about 3 g of Vitamin B3. In some embodiments, the composition includes about 200 μg to about 3 g of Vitamin C. In some embodiments, the composition includes about 1000 μg to about 3000 μg of folic acid.

The weight ratio between isoquercetin, vitamin B3, vitamin C, and folic acid in a composition of the invention can be 1:0.02-1:0.2-2.5, or any ratio in between. For example, the weight ratio can be 1:0.04-0.5:0.3-2.0, 1:0.05-0.3:0.4-1.5, 1:0.05-0.2:0.5-1, and 1:0.1-0.2:0.5-1. Preferred ratios include about 1:0.02:1, about 1:0.04:1, about 1:0.08:1, about 1:0.05:1.5, and about 1:0.16:1. Typically, a subject can be administered, once or periodically per day, with the composition in an amount that provides 100 mg to 2 g (preferably, 250 mg to 1 g) of isoquercetin.

After digestion, isoquercetin derivatives are converted to quercetin aglycon and other active derivatives, which are absorbed in the body. The quantity of isoquercetin mentioned above refers to that of quercetin aglycon or the quercetin moiety of an quercetin derivative. Isoquercetin can be added to a composition either in a pure form or as an ingredient in a mixture (e.g., a plant extract). Examples of commercially available isoquercetin include QU995 (containing 99.5% quercetin) and QU985 (containing 98.5% quercetin) from Quercegen Pharmaceuticals LLC (Boston, Mass.). Examples of commercially available isoquercetin include ISQ950AN (containing greater than or equal to 95% isoquercetin) and ISQ995AN (containing 99.5% isoquercetin) from Quercis Pharma AG (Zug, Switzerland)

Compositions of this invention can be in various forms including but not limited to soft chews, capsules, tablets and the like. For example, a composition may be a soft chew composition that includes isoquercetin, niacinamide, ascorbic acid, sodium ascorbate, sugar, corn syrup, sucralose, soy lecithin, corn starch, clycerin, palm oil, xylitol, carrageenan, FD&C Yellow #6, FD&C Yellow #5, and natural and/or artificial flavors. An exemplary serving of this soft chew composition (5.15 g) includes 250 mg of isoquercetin, 12.9 mg of vitamin B3 (i.e., niacinamide), and 382.8 mg vitamin C (i.e., L-ascorbic acid and sodium ascorbate). Folic acid may be provided in the soft chew or separately in an amount of about 1000 μg to about 3000 μg. A subject can take one to eight servings (e.g., 4 servings) of this soft chew composition daily. The amounts taken can vary depending on, for example, the disorder or condition to be treated and the physical states of the subject. Another exemplary composition of this soft chew includes 5.25 wt % of isoquercetin, 0.25 wt % of vitamin B3, and 7.81 wt % of vitamin C (i.e., L-ascorbic acid and sodium ascorbate).

Compositions of this invention can further contain one or more active ingredients, such as an isoflavone (e.g., genistein or genistin), curcumin, resveratrol, isoquercetin, luteolin, epigallocatechin gallate (EGCG), CoQ10, eicosapentaenoic acid (EPA), and docosahexaenoic acid (DHA). These active ingredients can be added to the composition either in a pure form or as a component in a mixture (e.g., an extract from a plant or an animal). A suitable daily dosage of each of these ingredients can vary depending on, for example, the disorder or condition to be treated and the physical states of the subjects. Exemplary daily dosages of some of these ingredients are: 20-2,500 mg (preferably 250-1,000 mg) of curcumin, 10-1,000 mg (preferably 100-500 mg) of resveratrol, 10-1,000 mg (preferably 100-250 mg) of isoquercetin, 50-1,000 mg (preferably 100-700 mg) of EGCG, 25-300 mg (preferably 50-100 mg) of genistin/genistein, 10-1,000 mg (preferably 100-200 mg) of luteolin, 50-1,000 mg (preferably 70-500 mg) of EPA, and 50-1,000 mg (preferably 80-700 mg) of DHA. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose. The composition can also contain amino acids, fatty acids, proteins, fibers, minerals, a flavor enhancer, or a coloring agent. Exemplary amino acids include glycine, alanine, valine, leucine, isoleucine, proline, serine, threonine, cysteine, methionine, phenylalanine, tyrosine, tryptophan, aspartate, glutamate, histidine, lysine, arginine and their L- and D-configurations. Amino acids may be added to aid in digestion. Exemplary fatty acids include but are not limited to omega-3 fatty acids (e.g., linolenic acid), omega-6 fatty acids (e.g., linoleic acid), omega-9 fatty acids (e.g., oleic acid), sunflower oil, sunflower lecithin, soy oil, and soy lecithin. Exemplary proteins include plant proteins, such as soy proteins and chia seed proteins. Exemplary fibers include plant fibers, such as soy fibers and chia seed fibers. These ingredients can be added in the above-described composition either in a pure form or as a component in a mixture (e.g., an extract from a plant or an animal).

In some examples, pharmaceutical compositions can further comprise one or more exemplary fillers. Examples of exemplary fillers include cellulose and cellulose derivatives such as microcrystalline cellulose; starches such as dry starch, hydrolyzed starch, and starch derivatives such as corn starch; cyclodextrin; sugars such as powdered sugar and sugar alcohols such as lactose, mannitol, sucrose and sorbitol; inorganic fillers such as aluminum hydroxide gel, precipitated calcium carbonate, carbonate, magnesium aluminometasilicate, dibasic calcium phosphate; and sodium chloride, silicon dioxide, titanium dioxide, titanium oxide, dicalcium phosphate dihydrate, calcium sulfate, alumina, kaolin, talc, or combinations thereof. Fillers may be present in the composition from about 20 wt % to about 65 wt %, about 20 wt % to about 50 wt %, about 20 wt % to about 40 wt %, about 45 wt % to about 65 wt %, about 50 wt % to about 65 wt %, or about 55 wt % to about 65 wt % of the total weight of the composition, or any value between these ranges.

In some examples, pharmaceutical compositions further comprise one or more disintegrants. Examples of disintegrants include starches, alginic acid, crosslinked polymers such as crosslinked polyvinylpyrrolidone, croscarmellose sodium, potassium starch glycolate, sodium starch glycolate, clays, celluloses, starches, gums, or combinations thereof. Disintegrants may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some examples, pharmaceutical compositions further comprise one or more binders, including but not limited to celluloses such as hydroxypropylcellulose, methyl cellulose, and hydroxypropylmethylcellulose; starches such as corn starch, pregelatinized starch, and hydroxypropyl starch; waxes and natural and synthetic gums such as acacia, tragacanth, sodium alginate; synthetic polymers such as polymethacrylates and polyvinylpyrrolidone; and povidone, dextrin, pullulane, agar, gelatin, tragacanth, macrogol, or combinations thereof. Binders may be present in the composition from about 0.5 wt % to about 5 wt %, about 0.5 wt % to about 4 wt %, about 0.5 wt % to about 3 wt %, about 0.5 wt % to about 2 wt %, or about 0.5 wt % to about 1 wt % of the total weight of the composition, or any value between these ranges.

In some examples, pharmaceutical compositions further comprise one or more wetting agents, including but not limited to oleic acid, glyceryl monostearate, sorbitan monooleate, sorbitan monolaurate, triethanolamine oleate, polyoxyethylene sorbitan mono-oleate, polyoxyethylene sorbitan monolaurate, sodium oleate, sodium lauryl sulfate, poloxamers, poloxamer 188, polyoxyethylene ethers, polyoxyethylene sorbitan fatty acid esters, polyoxyethylene fatty acid esters, polyethylene glycol fatty acid esters, polyoxyethylene hardened castor oil, polyoxyethylene alkyl ethers, polysorbates, cetyl alcohol, glycerol fatty acid esters (for example, triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and combinations thereof. Wetting agents may be present in the composition from about 0.1 wt % to about 1 wt %, about 0.1 wt % to about 2 wt %, about 0.1 wt % to about 3 wt %, about 0.1 wt % to about 4 wt %, or about 0.1 wt % to about 5 wt % of the total weight of the composition, or any value between these ranges.

In some examples, pharmaceutical compositions further comprise one or more lubricants, including but not limited to stearic acid, magnesium stearate, calcium hydroxide, talc, corn starch, sodium stearyl fumarate, alkali-metal and alkaline earth metal salts, waxes, boric acid, sodium benzoate, sodium acetate, sodium chloride, leucine, polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof. Lubricants may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some examples, the pharmaceutical composition further comprises one or more glidants, including but not limited to colloidal silicon dioxide, talc, sodium lauryl sulfate, native starch, and combinations thereof. Glidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some examples, pharmaceutical compositions can be a tablet and further comprise a topcoat, such as but not limited to, hydroxypropyl-methylcellulose coating or polyvinyl alcohol coating, and are available under the trade name Opadry, such as Opadry White, Opadry II (Opadry is a registered trademark of BPSI Holdings LLC, Wilmington, DE, USA). Topcoats may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some examples, pharmaceutical compositions can further comprise one or more preservative agents. Examples of preservative agents include but are not limited to sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, or combinations thereof. Preservative agents can be included in the liquid dosage form. The preservative agents can be in an amount sufficient to extend the shelf-life or storage stability, or both, of the liquid dosage form. Preservatives may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some examples, pharmaceutical compositions can further comprise one or more flavoring agents. Examples of flavoring agents include but are not limited to synthetic flavor oils and flavoring aromatics and/or natural oils, extracts from plants leaves, flowers, fruits, and so forth and the like or any combinations thereof. Additional examples include cinnamon oil, oil of wintergreen, peppermint oils, clove oil, bay oil, anise oil, *eucalyptus*, thyme oil, cedar leaf oil, oil of nutmeg, oil of sage, oil of bitter almonds, and *cassia* oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Flavoring agents may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

The pharmaceutical compositions can generally be in any physical form suitable for use in treating a subject. These forms can be referred to as a unit dosage form, such as an individual pill or tablet. In some examples, the pharmaceutical compositions can be formulated as tablets, capsules, granules, powders, liquids, suspensions, gels, syrups, slurries, suppositories, patches, nasal sprays, aerosols, injectables, implantable sustained-release formulations, or mucoadherent films. In some examples, the pharmaceutical compositions may be formed as a tablet, a bi-layer tablet, a capsule, a multiparticulate, a drug coated sphere, a matrix tablet, or a multicore tablet. A physical form can be selected according to the desired method of treatment.

The pharmaceutical compositions can be manufactured by various conventional methods such as conventional mixing, dissolving, granulating, dragee-making, levigating, emulsifying, encapsulating, entrapping, or lyophilizing processes. Pharmaceutical compositions can be formulated in a conventional manner using one or more physiologically acceptable carriers, diluents, excipients or auxiliaries that facilitate processing of the active agent into preparations that can be used pharmaceutically. Proper formulation can be selected upon the route of administration chosen.

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The compositions of this invention can be a dietary supplement or a pharmaceutical formulation. As a dietary supplement, additional nutrients, such as minerals or amino acids may be included. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soybean product (e.g., tofu), and rice products.

Method of Treating Sickle Cell Disease

In some embodiments, a method of treating sickle cell disease, wherein the method comprises administering to a patient in need thereof a therapeutically effective amount of isoquercetin, vitamin B3, and vitamin C. In some embodiments, a method of treating sickle cell disease, wherein the method comprises administering to a patient in need thereof a therapeutically effective amount of isoquercetin, vitamin B3, vitamin C, wherein the composition further comprises folic acid.

Diagnosis of sickle cells disease is based on the presence of sickle hemoglobin or another abnormal hemoglobin, such as SC, Sβ thalassemia, and SE or by genetic testing. Use of the described methods and pharmaceutical compositions can result in a reduction or elimination of disease, symptom, or other undesired property in a subject relative to a control population (for example, without treatment by the described methods and materials). Use of the described methods and pharmaceutical compositions can result cessation in the progression of the disease, symptom, or other undesired property in a subject relative to a control population. The reduction can generally be reduced by any amount. For example, the reduction can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and in an ideal situation, about 100% reduction (complete elimination of disease, symptom, virus concentration, or other undesired property).

In some embodiments, a method of treating sickle cell disease comprises inhibiting or preventing cytokine production in a patient, the method comprising administering a therapeutically effective amount of isoquercetin, vitamin B3, vitamin C, and optionally folic acid. In some embodiments, a method of treating sickle cell disease, wherein the method comprises administering to a patient or subject in need thereof a therapeutically effective amount of isoquercetin, vitamin B3, vitamin C, and optionally folic acid, wherein the method of treating results in at least one of the following: reduction anemia, fatigue, jaundice, painful swelling of the hands and feet (known as dactylitis), acute chest syndrome, acute pain crisis, sickle cell pain crisis, uncomplicated pain crisis, chronic pain, delayed growth or delayed puberty, eye problems (such as detached retina), hospitalizations, emergency room visits, and blood transfusions. In some embodiments, a method of treating sickle cell disease, wherein the method comprises administering to a patient or subject in need thereof a therapeutically effective amount of isoquercetin, vitamin B3, vitamin C, and optionally folic acid, wherein the method of treating results in at least one of the following severe anemia complications: aplastic crisis and splenic sequestration crisis.

The method of treating sickle cell disease, wherein the method comprises administering to a patient in need thereof a therapeutically effective amount of isoquercetin, vitamin B3, vitamin C, wherein the composition further comprises folic acid reduces P-selectin levels, platelet-dependent thrombin generation (coagulation), sE-selectin (adhesion)-biomarker, and C-reactive protein CRP.

The method described above can be preliminarily screened for efficacy in treating the above-described conditions by in vitro assays and then confirmed by animal experiments and clinic trials. Other suitable analytical and biological assays are apparent to those of ordinary skill in the art. For example, the bioavailability of isoquercetin can be measured by conducting pharmacokinetic studies and evaluated by the area under the curve in a plasma-drug concentration time curve.

The compounds and pharmaceutical compositions described herein may be administered at therapeutically effective dosage levels to treat the recited conditions, disorders, and diseases.

The compounds and pharmaceutical compositions described herein may be administered at prophylactically effective dosage levels to mitigate or prevent the recited conditions, disorders, and diseases.

The administration can be conducted daily for several days (for example about 2 to about 7 days), for several weeks (for example about 1 to about 4 weeks, specifically about 2 or about 3 weeks), or for several months (for example about 1 to about 36 months, specifically about 2 to about 24 months, and yet more specifically about 6 to about 12 months).

A therapeutically effective amount may range from about 0.001 pg/kg/day to about 500 mg/kg/day, preferably 0.01 pg/kg/day and 100 mg/kg/day. The skilled artisan will appreciate that certain factors may influence the dosage required to effectively treat a patient, including but not limited to the severity of the disease or disorder, previous treatments, the general health and/or age of the patient, and other diseases present. Moreover, treatment of a patient with a therapeutically effective amount of the compound can include a single treatment or, can include a series of treatments. It will also be appreciated that the effective dosage of a compound used for treatment may increase or decrease over the course of a particular treatment.

The method of administering an effective amount of isoquercetin, vitamin B3, vitamin C, optionally folic acid can occur once, twice, or three times a day to the patient in need thereof. Within this embodiment, the administration can be made orally.

Administration may be performed by generally any method. Methods of administering include infusion or injection of the composition. Example delivery methods of administering include topical delivery, subcutaneous delivery, intravenous injection (IV) delivery, intramuscular injection (IM) delivery, intrathecal injection (IT) delivery, intraperitoneal injection (IP) delivery, transdermal delivery, subcutaneous delivery, oral delivery, transmucosal oral delivery, pulmonary delivery, inhalation delivery, intranasal delivery, buccal delivery, rectal delivery, vaginal delivery, and combinations thereof. In some embodiments, the administering comprises oral delivery.

For injection, pharmaceutical compositions can be formulated in aqueous solutions, preferably in physiologically compatible buffers such as Hanks solution, Ringer's solution, or physiological saline buffer and/or in certain emulsion formulations. Solutions can contain one or more formulatory agents such as suspending, stabilizing and/or dispersing agents. In certain examples the pharmaceutical compositions can be provided in powder form for constitution with a suitable vehicle, for example, sterile pyrogen-free water, before use. For transmucosal administration, one or more penetrants appropriate to the barrier to be permeated can be used in the formulation. Such penetrants are generally known in the art.

For oral administration the composition may be formulated as tablets, pills, dragees, capsules, liquids, gels, syrups, slurries, suspensions and the like, for oral ingestion by a patient to be treated. For oral solid formulations such as, for example, the compositions may take the form of powders, capsules and tablets. For buccal administration, the compositions may take the form of tablets, lozenges, etc. formulated in conventional manner.

For administration by inhalation, the pharmaceutical composition can be delivered in the form of an aerosol spray from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The subject can generally be any mammal. Examples of subjects include a primate, a human, a dog, a cat, a mouse, a rat, a cow, a horse, a pig, a rabbit, and a ferret. In some examples, the subject is a human. The terms "subject", "individual", or "patient" are used interchangeably and as used herein are intended to include human and non-human animals. Non-human animals include all vertebrates, for example, mammals and non-mammals, such as non-human primates, sheep, dogs, rats, cats, cows, horses, ferrets, chickens, amphibians, and reptiles. Examples of mammals include non-human primates, sheep, dogs, cats, cows, ferrets, and horses.

EXAMPLES

Example 1: Isoquercetin in Sickle Cell Anemia

Brief Summary: This research study is being done to assess the safety and effectiveness of isoquercetin to reduce levels of soluble P-Selectin in patients with sickle cell disease. Isoquercetin is a naturally occurring flavonoid—or vitamin. You will find quercetin and isoquercetin in fruits and vegetables. The names of the study drug involved in this study are/is: isoquercetin.

Detailed Description: This is a single-arm phase 2 study in adults with Sickle Cell Disease (SCD) to assess the effect of oral isoquercetin on biomarkers of endothelial and platelet activation, inflammation and ongoing blood coagulation. The research study procedures include screening for eligibility and study treatment including evaluations and follow up visits. The names of the study drug involved in this study are/is: Isoquercetin. Participants will receive study treatment for 1 year and will be followed for 30 days after the last dose. This research study is a Phase II clinical trial. Phase II clinical trials test the safety and effectiveness of an investigational drug to learn whether the drug works in treating a specific disease. "Investigational" means that the drug is being studied. The U.S. Food and Drug Administration (FDA) has not approved isoquercetin as a treatment for any disease.

Study Design: Interventional Clinical Trial

TABLE 1

| Study Design | |
| --- | --- |
| Study Type | Interventional (Clinical Trial) |
| Interventional Model | Single Group Assignment |
| Masking | None (Open Label) |
| Primary Purpose | Treatment |
| Official Title | Single-arm Phase 2 Study of Oral Isoquercetin in Sickle Cell Disease |

TABLE 2

| Arms and Interventions | |
| --- | --- |
| Arm | Intervention/Treatment |
| Experimental: Isoquercetin The research study procedures include screening for eligibility and study treatment includes evaluations and follow up visits. Isoquercetin: Oral Study Drug, 1 time per day, per predetermined dosed per 28 treatment cycle. This will continue for up to 337 days. | Drug: Isoquercetin Oral, 1 time per day, per predetermined dosed per 28 treatment cycle. |

Primary Outcome Measures: Change in sP Selectin levels with isoquercetin (Time Frame: baseline to 28 Days). Comparisons between baseline and follow-up measurements (i.e. change in sP-Selectin), will be performed using a two-tailed, paired t-test analyses.

Secondary Outcome Measures: 1) Platelet dependent thrombin generation (coagulation) (Time Frame: baseline to 1 year). Laboratory values at baseline and subsequent monthly follow-up time points will be modeled using linear mixed effects regression with an autoregressive covariance structure. 2) sE-selectin (adhesion)-Biomarker (Time Frame: baseline to 1 year). 3) C-reactive protein CRP (Time Frame: baseline to 1 year). Laboratory values at baseline and subsequent monthly follow-up time points will be modeled using linear mixed effects regression with an autoregressive covariance structure. 4) Number of Participants With Treatment-Related Adverse Events (Time Frame: start of study treatment up to 13 months). Sickle cell events such as sickle cell pain crisis, uncomplicated pain crisis, hospitalizations, emergency room visits, transfusions, acute chest syndrome and transfusion support will be summarized as annualized numbers. Statistical comparisons will be made for each patient relative to the number from the previous year using a Wilcoxon rank-sum test.

Eligibility Criteria: Ages Eligible for Study: 18 years to 50 Years (Adult). Sexes Eligible for Study: All. Accepts Healthy Volunteers: Yes.

Inclusion Criteria: Eligible subjects require an established diagnosis of sickle cell disease/homozygous hemoglobin S (SCD-SS) or sickle cell disease hemoglobin β0-thalassemia (SCD-Sβ0-thal). Patients on other therapy including hydroxyurea will be included. Age 18-50 years. Participants must have preserved organ and marrow function as defined: leukocytes≥2,000/mcL, platelets≥75,000/mcL, AST (SGOT)/ALT(SGPT)≤2.5×institutional upper limit of normal, estimated creatinine clearance ≥45 mL/min/1.73 m2 for participants with creatinine levels above institutional normal. Subjects with no evidence of worsening over the last 4 weeks (e.g. any acute complication of SCD including but not limited to VOC, acute chest syndrome and stroke, that required unscheduled medical attention or intervention) as determined by the investigator will be included. Patients on anticoagulation therapy will be excluded. The effects of isoquercetin on the developing human fetus are unknown. For this reason, women of child-bearing potential and men must agree to use adequate contraception (hormonal or barrier method of birth control; abstinence) prior to study entry and for the duration of study participation. Should a woman become pregnant or suspect she is pregnant while she or her partner is participating in this study, she should inform her treating physician immediately. Men treated or enrolled on this protocol must also agree to use adequate contraception prior to the study, for the duration of study participation, and 4 months after completion of isoquercetin administration. Ability to understand and the willingness to sign a written informed consent document.

Exclusion Criteria: Please ensure exclusion criteria are clearly worded to describe participants who will not be eligible. Participants may not be concurrently receiving any other study agents. Subjects with no evidence of worsening over the last 1 month (e.g. any acute complication of SCD including but not limited to VOC, acute chest syndrome and stroke, that required unscheduled medical attention or intervention) as determined by the investigator will be included. Familial bleeding diathesis. Known diagnosis of disseminated intravascular coagulation. Currently receiving anticoagulant therapy. Currently using daily use of aspirin (>81 mg daily), Clopidogrel (Plavix), cilostazol (Pletal), aspirin-dipyridamole (Aggrenox) (within 10 days). History of allergic reactions attributed to compounds of similar chemical or biologic composition to isoquercetin. Uncontrolled intercurrent illness including but not limited to ongoing or active infection, symptomatic congestive heart failure, unstable angina, cardiac arrhythmia, or psychiatric illness/social situations that would limit study compliance. Pregnant women are excluded from this study because isoquercetin is a PDI inhibitor with the potential for teratogenic or abortifacient effects. Because there is an unknown but potential risk of adverse events in nursing infants secondary to treatment of the mother with isoquercetin, breastfeeding should be discontinued if the mother is treated with isoquercetin. These potential risks may also apply to other agents used in this study.

What is claimed is:

1. A method of treating one or more symptoms of sickle cell disease in a subject in need thereof, the method comprising administering to the subject a composition comprising an effective amount of isoquercetin, vitamin B3, and vitamin C,
thereby treating the one or more symptoms of sickle cell disease,
wherein the subject is not currently receiving anticoagulant therapy; and
wherein the one or more symptoms of sickle cell disease are selected from the group consisting of anemia, fatigue, jaundice, painful swelling of the hands and feet, acute chest syndrome, acute pain crisis, sickle cell pain crisis, uncomplicated pain crisis, chronic pain, delayed growth or delayed puberty, eye problems, detached retina, hospitalizations, emergency room visits, and blood transfusions, or any combination thereof.

2. The method of claim 1, wherein the composition further comprises folic acid.

3. The method of claim 2, wherein the composition comprises about 1000 µg to about 3000 µg of folic acid.

4. The method of claim 1, wherein the composition comprises about 250 mg to about 2500 mg of isoquercetin.

5. The method of claim 1, wherein the composition comprises about 20 µg to about 3 g of Vitamin B3.

6. The method of claim 1, wherein the composition comprises about 200 µg to about 3 g of Vitamin C.

7. The method of claim 1, wherein administering the composition reduces one or more of P-selectin, platelet-dependent thrombin generation, sE-selectin, or C-reactive protein.

8. The method of claim 4, wherein the composition comprises about 250 mg to about 1000 mg of isoquercetin.

9. A method of treating sickle cell disease in a subject in need thereof, the method comprising administering to the subject a composition comprising:
isoquercetin present from about 250 mg to 2500 mg;
vitamin B3 present from about 20 µg to 3 g; and
vitamin C present from about 200 µg to 3 g;
wherein administering the composition reduces one or more of P-selectin, platelet-dependent thrombin generation, sE-selectin, or C-reactive protein.

10. A method of treating one or more symptoms of sickle cell disease in a subject in need thereof, the method comprising administering to the subject a composition comprising:
isoquercetin present from about 250 mg to 1000 mg;
vitamin B3 present from about 200 µg to about 3 g; and
vitamin C present from about 200 µg to about 3 g,
wherein the one or more symptoms of sickle cell disease are selected from the group consisting of anemia, fatigue, jaundice, painful swelling of the hands and feet, acute chest syndrome, acute pain crisis, sickle cell pain crisis, uncomplicated pain crisis, chronic pain, delayed growth or delayed puberty, eye problems, detached retina, hospitalizations, emergency room visits, and blood transfusions, or any combination thereof.

11. The method of claim 9 or 10, the composition further comprising about 1000 µg to about 3000 µg of folic acid.

* * * * *